(12) United States Patent
Castile

(10) Patent No.: US 8,520,288 B2
(45) Date of Patent: Aug. 27, 2013

(54) METHOD AND APPARATUS FOR RESONANT GAS PHASE ACOUSTO-OPTIC MODULATION

(75) Inventor: Brett Castile, Del Mar, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 247 days.

(21) Appl. No.: 13/114,708

(22) Filed: May 24, 2011

(65) Prior Publication Data

US 2012/0300281 A1    Nov. 29, 2012

(51) Int. Cl.
*G02F 1/11* (2006.01)

(52) U.S. Cl.
USPC .......................................................... 359/285

(58) Field of Classification Search
USPC .......................................................... 359/285
See application file for complete search history.

(56) References Cited

U.S. PATENT DOCUMENTS

| | | | |
|---|---|---|---|
| 3,602,577 | A | 8/1971 | Byram |
| 3,656,068 | A | 4/1972 | Runge |
| 3,675,150 | A | 7/1972 | Harris et al. |
| 4,019,155 | A | 4/1977 | Gorog et al. |
| 4,460,250 | A | 7/1984 | Freyre et al. |
| 6,924,895 | B2 | 8/2005 | Chovan et al. |
| 7,697,195 | B2 * | 4/2010 | Hill .............................. 359/305 |
| 2008/0151351 | A1 | 6/2008 | Herz |

* cited by examiner

*Primary Examiner* — James Jones

(74) *Attorney, Agent, or Firm* — Ronald E. Prass, Jr.; Prass LLP

(57) ABSTRACT

A method and apparatus for resonant gas phase optical phase modulation is disclosed. The method may include passing a laser beam longitudinally through a tube open to air at both ends and setting air inside the tube into resonant acoustic oscillation, thereby temporally modulating the refractive index of the air, which temporally modulates the optical phase of the laser beam.

21 Claims, 4 Drawing Sheets

METHOD AND APPARATUS FOR RESONANT GAS PHASE ACOUSTO-OPTIC MODULATION

BACKGROUND

1. Field of the Disclosed Embodiments

The disclosure relates to resonant gas phase acousto-optic modulation.

2. Introduction

Optical phase modulators of various types are commercially available. However, they are not optimum for many uses including use in a self-diffraction densitometer incorporating an optical homodyne. Existing optical phase modulators generally use an electro-optic crystal. This presents optical surfaces through which an optical beam must pass. Because many potential uses for optical phase modulators may be in systems that ultimately need to detect optical beams of miniscule amplitude, it is important to minimize the number of optical surfaces through which beams to be modulated pass.

Electro-optic crystal optical phase modulators used currently also inevitably scatter some of the monochromatic laser light. Further, existing solid state optical phase modulators inevitably produce some, although small, residual amplitude modulation.

Thus, a need exists for an optical modulator that presents no optical surfaces through which a beam passes and therefore keeps spurious scattering to a minimum and may be used to improve, among other things, self-diffraction densitometers.

SUMMARY OF THE DISCLOSED EMBODIMENTS

A method and apparatus for resonant gas phase optical phase modulation is disclosed. The method may include passing a laser beam longitudinally through a tube open to air at both ends and setting air inside the tube into resonant acoustic oscillation, thereby temporally modulating the refractive index of the air, which temporally modulates the optical phase of the laser beam.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION OF THE DISCLOSED EMBODIMENTS

Additional features and advantages of the disclosure will be set forth in the description which follows, and in part will be obvious from the description, or may be learned by practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth herein.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

Aspects of the embodiments disclosed herein relate to a method for resonant gas phase optical phase modulation, as well as corresponding apparatus and computer-readable medium.

The disclosed embodiments may include a method for resonant gas phase optical phase modulation. The method may include passing a laser beam longitudinally through a tube open to air at both ends and setting air inside the tube into resonant acoustic oscillation, thereby temporally modulating the refractive index of the air, which temporally modulates the optical phase of the laser beam.

The disclosed embodiments may include an apparatus for resonant gas phase optical phase modulation. The apparatus may a tube open to air at both ends through which a laser beam is passed longitudinally and an acoustic transducer within the tube to set air inside the tube into resonant acoustic oscillation, thereby temporally modulating the refractive index of the air and thus temporally modulating the optical phase of the laser beam.

The disclosed embodiments may include a non-transient computer-readable medium storing instructions for resonant gas phase optical phase modulation, the instructions comprising passing a laser beam longitudinally through a tube open to air at both ends and setting air inside the tube into resonant acoustic oscillation, thereby temporally modulating the refractive index of the air, which temporally modulates the optical phase of the laser beam.

Figure 1:
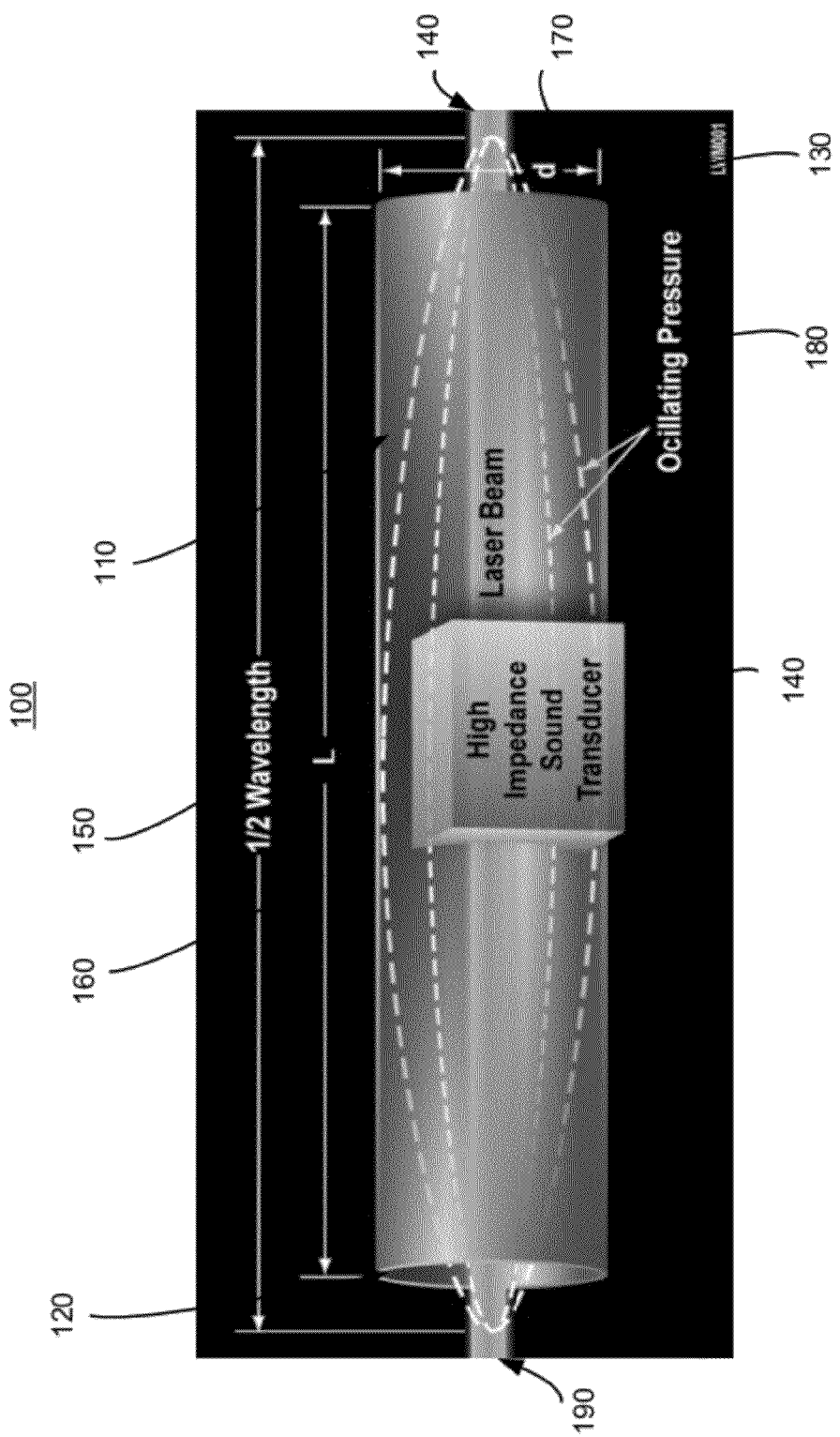
FIG. 1 is a is a diagram of an exemplary resonant gas phase acousto-optic modulator in accordance with a possible embodiment of the disclosure.

FIG. 1 is a is a diagram of an exemplary resonant gas phase acousto-optic modulator 100 which may be used in the self-diffraction densitometer incorporating an optical homodyne in accordance with a possible embodiment of the disclosure. It is understood that using the resonant gas phase acousto-optic modulator in a self-diffraction densitometer incorporating an optical homodyne is but one of anticipated possible uses for embodiments of the present disclosure.

The resonant gas phase acousto-optic modulator may include a tube 110 open to air at both ends 120, 130 through which a laser beam 140 is passed longitudinally. An acoustic transducer 140 within the tube may set air inside the tube 110 into resonant acoustic oscillation. The refractive index of air varies somewhat with air pressure. Thus, a laser beam 140 passing through the tube will have imposed on it a periodic sinusoidal phase modulation with the period of the acoustic resonance. The phase modulated beam is shown at 190 at the output of tube 210. As can be seen, the resonant gas phase acousto-optic modulator 100 presents no optical surfaces through which beam 148 must pass and therefore keeps spurious scattering to a minimum.

In an embodiment of the disclosure, the acoustic transducer may be near a center of the tube 110 and the acoustic transducer 140 may be used to excite the resonant acoustic oscillation within the tube 110 to create acoustic oscillations such that one acoustic wavelength 150 is slightly longer than twice the tube 110 length 160.

The acoustic pressure oscillates at high amplitude near the center of the tube 110 and tapers to near zero at both ends 120, 130 of the tube 110. The refractive index of the air inside the tube 110 varies periodically with air pressure, thereby imposing a sinusoidal phase modulation with a period of acoustic resonance on the laser beam passed lengthwise through the tube 110.

Figure 2:
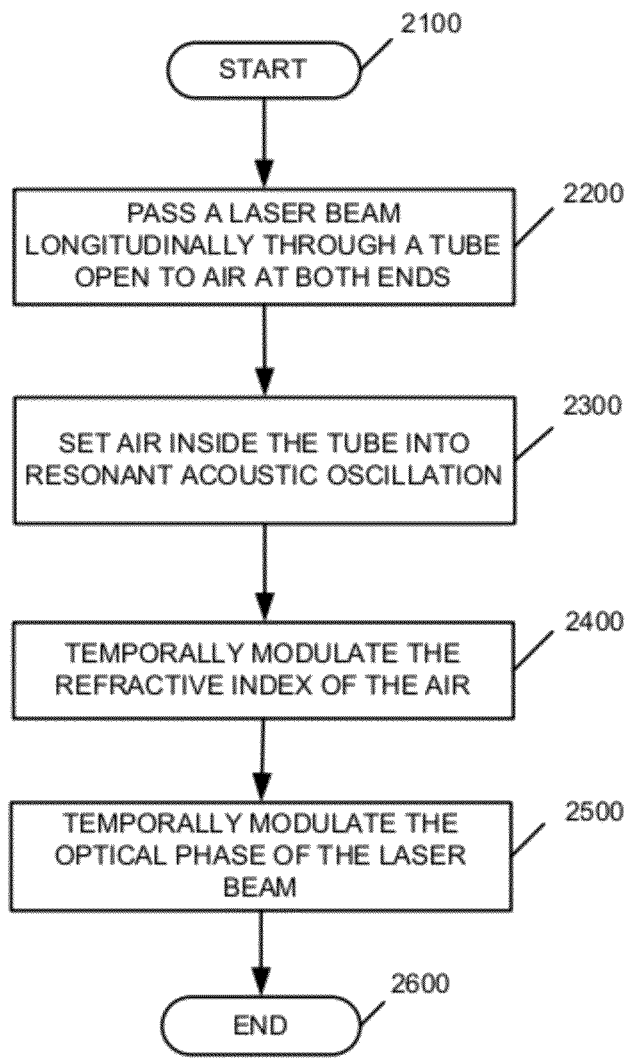
FIG. 2 is an exemplary flowchart illustrating the method of operation of a resonant gas phase acousto-optic in accordance with one possible embodiment of the disclosure.

FIG. 2 is an exemplary flowchart illustrating the method of operation of the resonant gas phase acousto-optic modulator in accordance with one possible embodiment of the disclosure. The process may begin at step 2100 and may continue to step 2200, where a laser beam is passed longitudinally through tube 110 open to air at both ends 120, 130.

At step 2300 air inside the tube 110 is set into resonant acoustic oscillation. At step 2400, the refractive index of the air is temporally modulated. At step 2500, the optical phase of the laser beam is thus temporally modulated.

Figure 3:
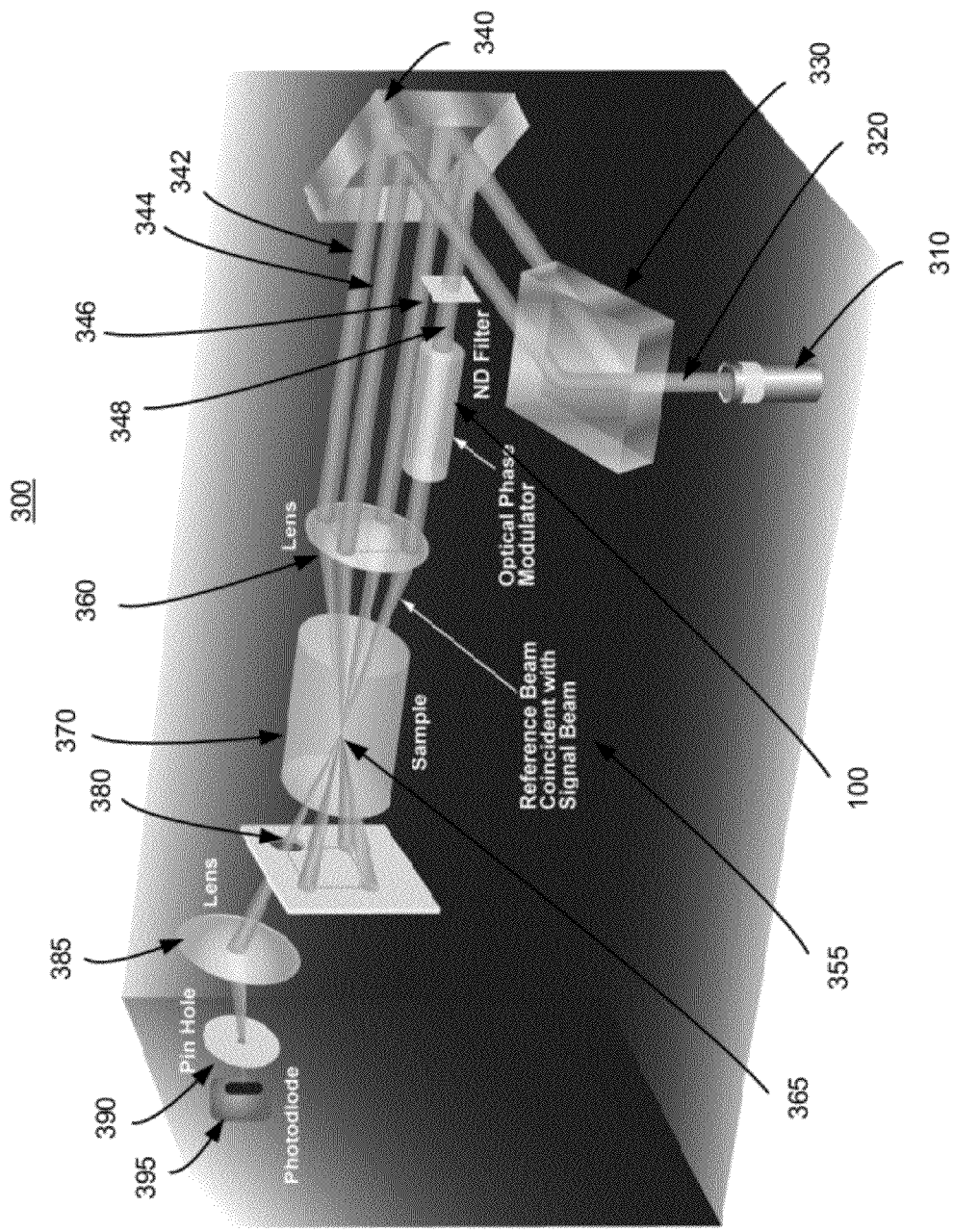
FIG. 3 is a diagram of an exemplary self-diffraction densitometer incorporating an optical homodyne in accordance with a possible embodiment of the disclosure.

FIG. 3 is a diagram of an exemplary self-diffraction densitometer incorporating an optical homodyne 300 that may use as the optical modulator 100 the resonant gas phase acousto-optic modulator of the present disclosure.

The self-diffraction densitometer incorporating an optical homodyne 300 may include a plurality of beam splitters 310, 340 for splitting laser beam 320 generated by laser 310 into four beams 342, 344, 346 and 348. These beams may be four inherently parallel beams.

A lens 360 may pass three beams 342, 344 and 346 of the four beams 342, 344, 346 and 348 to focus the three beams 342, 344 and 346 to minimum diffraction limited waist size and bring them to convergence at a convergence zone 365 containing an analyte 370. The beam convergence zone may contain a three dimensional interference pattern. A fourth beam 148 of the four beams 142, 144, 146 and 148 may pass through the resonant gas phase acousto-optic modulator 100 of the present invention to generate a reference beam 355.

If a medium within the convergence zone 365 absorbs energy at a wavelength of the laser beam 320, a thermal representation of an interference pattern forms and spatial modulation of temperature results in a spatial modulation of refractive index. In an embodiment of the present disclosure, a diffracted beam 380 from energy of the three beams 342, 344, 346 is produced into a propagation path of the reference beam 355.

The reference beam 355 passes through the lens 360 and the convergence zone 365 such that the reference beam 355 is coincident with the diffracted beam 380 and the reference beam 355 and diffracted beams 380 cyclically go in and out of relative phase. The reference beam 355 and the diffracted beam 380 impinge on an optical detector, which, in an embodiment of the disclosure, may be a photodiode 395.

A second lens 385 may be incorporated to concentrate and direct the reference 355 and diffracted 380 beams through a pin hole 390 prior to impinging the optical detector 395.

The resonant gas phase acousto-optic modulator 100 illustrated in FIG. 1 and self-diffraction densitometer incorporating an optical homodyne resonant gas phase acousto-optic modulator in FIG. 2 and associated method described in FIG. 3 and the related discussion were intended to provide a brief, general description of a suitable environment in which the invention may be implemented. Although not required, the invention is described below, at least in part, in the general context of computer-executable instructions, such as program modules, being executed by the resonant gas phase acousto-optic modulator 100, controlled by a general purpose computer, for example.

Generally, program modules include routine programs, objects, components, data structures, etc. that perform particular tasks or implement particular abstract data types. Moreover, those skilled in the art will appreciate that other embodiments of the invention may be practiced in communication network environments with many types of communication equipment and computer system configurations, including personal computers, hand-held devices, multi-processor systems, microprocessor-based or programmable consumer electronics, and the like.

Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Embodiments within the scope of the present disclosure may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Figure 4:
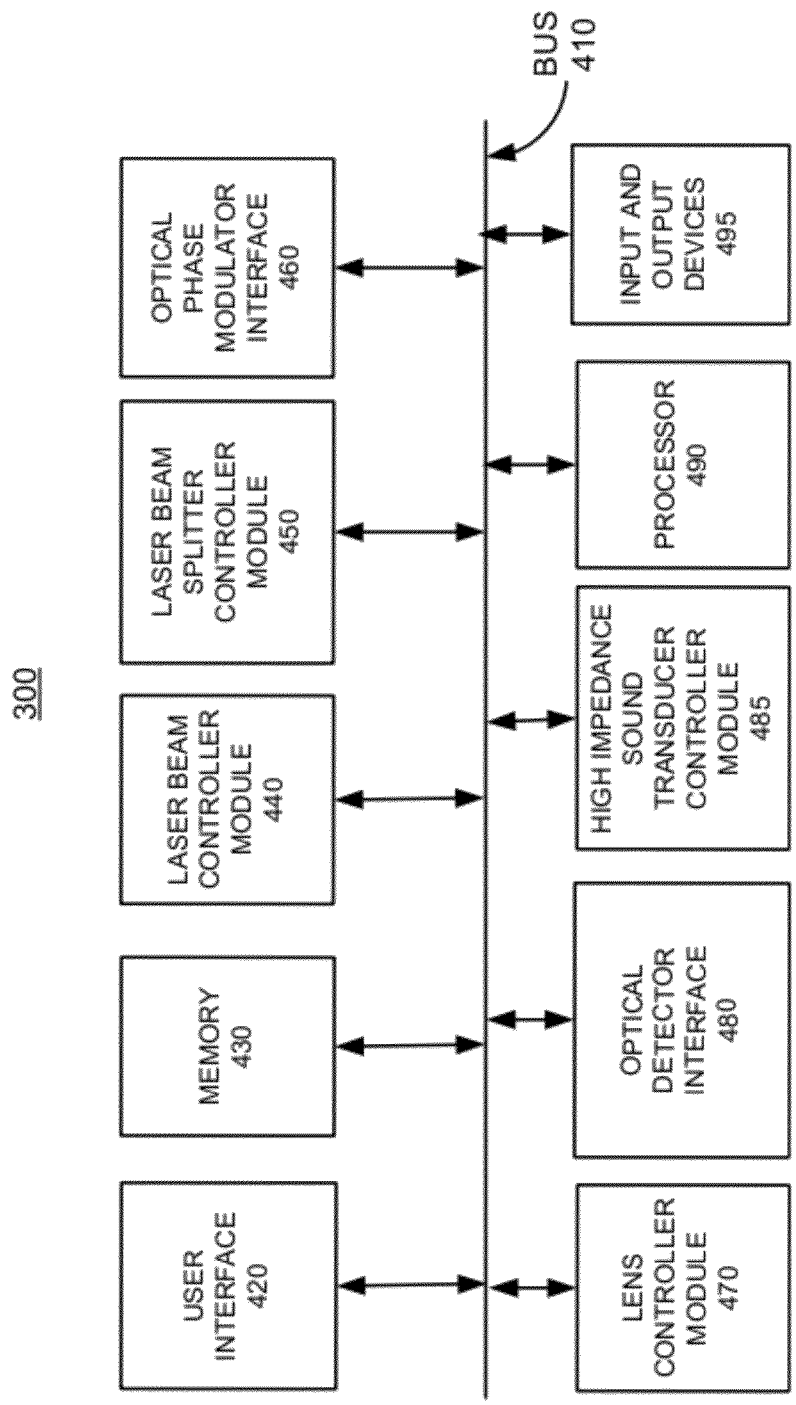
FIG. 4 is a block diagram of an exemplary resonant gas phase acousto-optic modulator incorporated into a self-diffraction densitometer incorporating an optical homodyne in accordance with a possible embodiment of the disclosure.

FIG. 4 is block diagram of a resonant gas phase acousto-optic modulator incorporated into a self-diffraction densitometer incorporating an optical homodyne 300 that may be controlled and operable in a computing environment in accordance with a possible embodiment. The resonant gas phase acousto-optic modulator 100 may include bus 410, user interface 420, memory 430, laser beam controller module 440, laser beam splitter controller module 450, optical phase modulator interface 460, lens controller module 470, optical detector interface 480, high impedance sound transducer controller module 485, processor 490 and input and output devices 495.

Processor 420 may include at least one conventional processor or microprocessor that interprets and executes instructions. Memory 430 may be a random access memory (RAM) or another type of dynamic storage device that stores information and instructions for execution by processor 420. Memory 430 may also include a read-only memory (ROM) which may include a conventional ROM device or another type of static storage device that stores static information and instructions for processor 420.

User interface 420 may enable interaction with and the ability to obtain information from resonant gas phase acousto-optic modulator 100 and self-diffraction densitometer 300, wherein which gas phase acousto-optic modulator 100 is operable. For example, information about resonant frequencies and performance of high impedance sound transducer 140.

ROM may be included in memory 430 to include a conventional ROM device or another type of static storage device that stores static information and instructions for processor 420. A storage device may augment the ROM and may include any type of storage media, such as, for example, magnetic or optical recording media and its corresponding drive.

Input devices 495 may include one or more conventional mechanisms that permit a user to input information to resonant gas phase acousto-optic modulator 100, such as a keyboard, a mouse, a pen, a voice recognition device, touchpad, buttons, etc. Output devices 495 may include one or more conventional mechanisms that output information to the user, including a display, a printer, a copier, a scanner, a multifunction device, one or more speakers, or a medium, such as a memory, or a magnetic or optical disk and a corresponding disk drive.

The resonant gas phase acousto-optic modulator 100 may perform such functions in response to processor 420 by executing sequences of instructions contained in a computer-readable medium, such as, for example, memory 430. Such instructions may be read into memory 430 from another computer-readable medium, such as a storage device or from a separate device via a communication interface.

Although the above description may contain specific details, they should not be construed as limiting the claims in any way. Other configurations of the described embodiments of the disclosure are part of the scope of this disclosure. For example, the principles of the disclosure may be applied to each individual user where each user may individually deploy such a system. This enables each user to utilize the benefits of the disclosure even if any one of the large number of possible applications do not need the functionality described herein. In other words, there may be multiple instances of the components each processing the content in various possible ways. It does not necessarily need to be one system used by all end users. Accordingly, the appended claims and their legal equivalents should only define the disclosure, rather than any specific examples given.

I claim:

1. A method for resonant gas phase optical phase modulation, comprising:
    passing a laser beam longitudinally through a tube open to air at both ends; and
    setting air inside the tube into resonant acoustic oscillation, thereby temporally modulating the refractive index of the air, which temporally modulates the optical phase of the laser beam,
    wherein the acoustic transducer used to excite the resonant acoustic oscillation within the tube creates acoustic oscillation such that one acoustic wavelength is slightly longer than twice the tube length.

2. The method of claim 1, further comprising using an acoustic transducer to set the air inside the tube into resonant acoustic oscillation.

3. The method of claim 2, wherein the acoustic transducer is near a center of the tube.

4. The method of claim 1, wherein acoustic pressure oscillates at high amplitude near the center of the tube and tapers to near zero at both ends of the tube.

5. The method of claim 1, wherein a refractive index of the air inside the tub varies periodically with air pressure, thereby imposing a sinusoidal phase modulation with a period of acoustic resonance on the laser beam passed lengthwise through the tube.

6. The method of claim 5, further comprising incorporating the gas phase optical phase modulation into an optical homodyne self-diffraction densitometer.

7. An apparatus for resonant gas phase optical phase modulation, comprising:
    a tube open to air at both ends through which a laser beam is passed longitudinally; and
    an acoustic transducer within the tube to set air inside the tube into resonant acoustic oscillation, thereby temporally modulating the refractive index of the air and temporally modulating the optical phase of the laser beam,
    wherein the acoustic transducer used to excite the resonant acoustic oscillation within the tube creates acoustic oscillation such that one acoustic wavelength is slightly longer than twice the tube length.

8. The apparatus of claim 7, wherein the acoustic transducer is near a center of the tube.

9. The apparatus of claim 7, wherein acoustic pressure oscillates at high amplitude near the center of the tube and tapers to near zero at both ends of the tube.

10. The apparatus of claim 7, wherein a refractive index of the air inside the tub varies periodically with air pressure, thereby imposing a sinusoidal phase modulation with a period of acoustic resonance on the laser beam passed lengthwise through the tube.

11. The apparatus of claim 10, wherein said apparatus is operable in an optical homodyne self-diffraction densitometer.

12. A resonant gas phase acousto-optic modulator, comprising:
    an open ended cylinder without optical surfaces through which a laser beam is passed longitudinally; and
    an acoustic transducer within the cylinder to set air inside the cylinder into resonant acoustic oscillation, thereby temporally modulating the refractive index of the air and thus temporally modulating an optical phase of the laser beam,
    wherein the acoustic transducer used to excite the resonant acoustic oscillation within the cylinder creates acoustic oscillation such that one acoustic wavelength is slightly longer than twice the cylinder length.

13. The resonant gas phase acousto-optic modulator of claim 12, wherein the acoustic transducer is near a center of the cylinder.

14. The resonant gas phase acousto-optic modulator of claim 12, wherein acoustic pressure oscillates at high amplitude near the center of the cylinder and tapers to near zero at both ends of the cylinder.

15. The resonant gas phase acousto-optic modulator of claim 12, wherein a refractive index of the air inside the cylinder varies periodically with air pressure, thereby imposing a sinusoidal phase modulation with a period of acoustic resonance on the laser beam passed lengthwise through the cylinder.

16. The resonant gas phase acousto-optic modulator of claim 15, wherein said apparatus is operable in an optical homodyne self-diffraction densitometer.

17. A non-transient computer-readable medium storing instructions for resonant gas phase optical phase modulation, the instructions comprising:
  passing a laser beam longitudinally through a tube open to air at both ends; and
  setting air inside the tube into resonant acoustic oscillation, thereby temporally modulating the refractive index of the air, which temporally modulates the optical phase of the laser beam,
  wherein the acoustic transducer used to excite the resonant acoustic oscillation within the tube creates acoustic oscillation such that one acoustic wavelength is slightly longer than twice the tube length.

18. The non-transient computer-readable medium of claim 17, further comprising:
  using an acoustic transducer to set the air inside the tube into resonant acoustic oscillation.

19. The non-transient computer-readable medium of claim 18, wherein the acoustic transducer is near a center of the tube.

20. The non-transient computer-readable medium of claim 17, wherein acoustic pressure oscillates at high amplitude near the center of the tube and tapers to near zero at both ends of the tube.

21. The non-transient computer-readable medium of claim 17, wherein a refractive index of the air inside the tub varies periodically with air pressure, thereby imposing a sinusoidal phase modulation with a period of acoustic resonance on the laser beam passed lengthwise through the tube.

\* \* \* \* \*